US005089422A

United States Patent [19]
Brubaker

[11] Patent Number: 5,089,422
[45] Date of Patent: Feb. 18, 1992

[54] VITRO BLEEDING TIME DETERMINATION

[75] Inventor: Daniel B. Brubaker, Redondo Beach, Calif.

[73] Assignee: Research and Education Institute, Inc., Torrance, Calif.

[21] Appl. No.: 529,112

[22] Filed: May 25, 1990

Related U.S. Application Data

[63] Continuation of Ser. No. 458,308, Dec. 28, 1989, abandoned, which is a continuation of Ser. No. 155,953, Feb. 12, 1988, abandoned.

[51] Int. Cl.$^5$ .................. G01N 11/04; G01N 33/48
[52] U.S. Cl. ................................. 436/69; 436/165; 436/809; 422/58; 422/73; 73/64.1
[58] Field of Search .............. 422/69, 73, 58, 61; 436/69, 165, 809; 73/57, 64.1

[56] References Cited

U.S. PATENT DOCUMENTS 4,599,219  7/1986  Cooper et al. ............... 422/73
4,604,894  8/1986  Kratzer et al. .............. 422/73

FOREIGN PATENT DOCUMENTS 2096329  9/1982  United Kingdom .

OTHER PUBLICATIONS

D. Brubaker, "An In Vitro Bleeding Time Test", Am. J. Clin. Path., 91,422 (1989).
M. A. A. Kratzer et al, "Streamline Pattern and Velocity Components of Flow in a Model of a Branching Coronary Vessel", Microvascular Res, 31,250 (1986).
Von Der Goltz advertisement entitled "In Vitro Blutungzeit."
"A Protocol for Cryoprecipate Production", Transfusion, Burka et al., vol. 15, No. 4, 1975 (p. 307).

Primary Examiner—David L. Lacey
Assistant Examiner—Kimberly A. Trautman
Attorney, Agent, or Firm—Drucker & Sommers

[57] ABSTRACT

An apparatus and method for in vitro bleeding time determination. Blood is placed in a tube having a window covered with a clot promoting material having a slit. The time required before blood stops flowing through the slit is recorded, and is the bleeding time. It is preferred that the clot-promoting material be nylon fabric impregnated with collagen and blood clot promoting proteins.

17 Claims, 1 Drawing Sheet

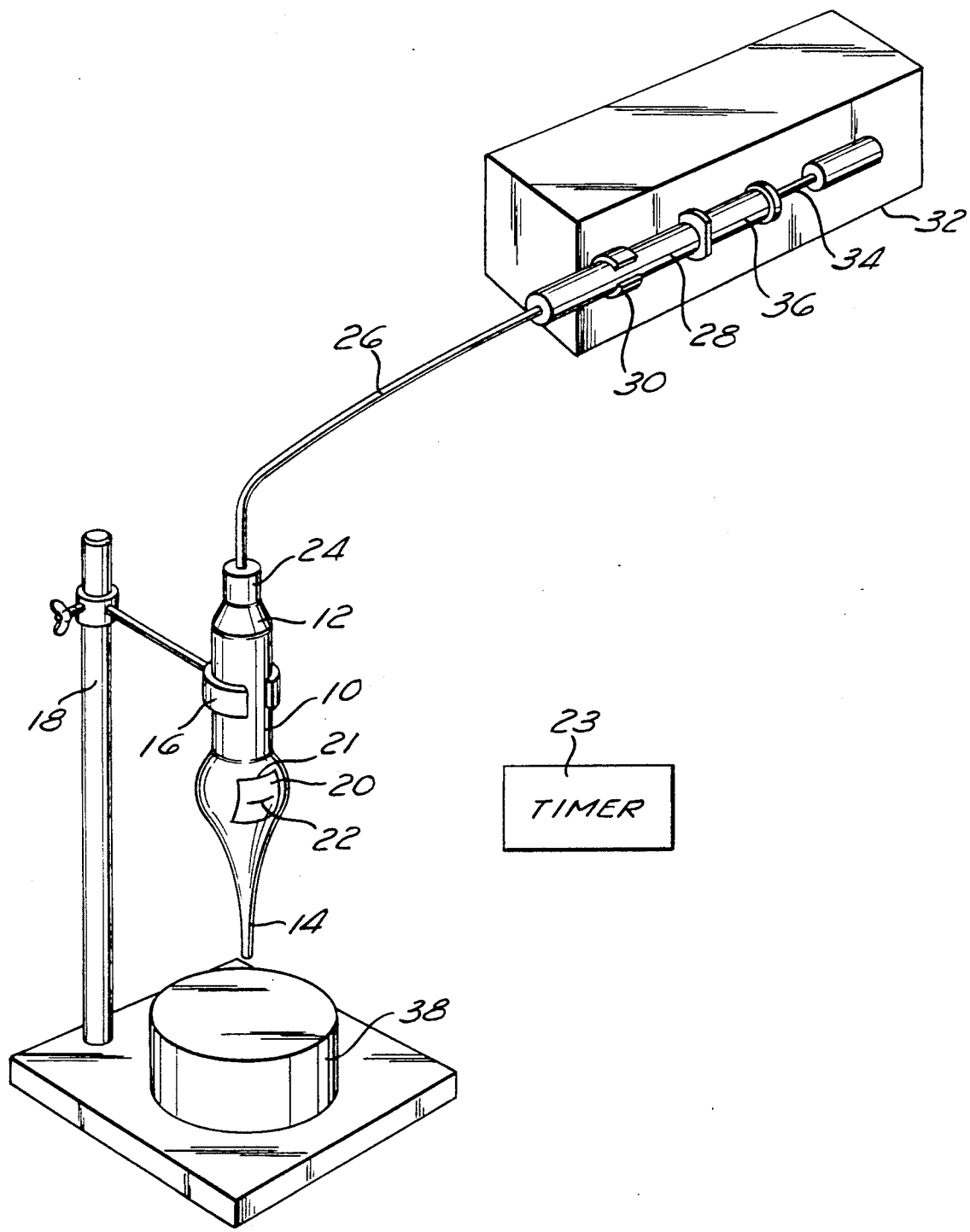

VITRO BLEEDING TIME DETERMINATION

CROSS REFERENCE TO RELATED APPLICATIONS

This is a continuation of application Ser. No. 07/458,308, filed Dec. 28, 1989, now abandoned, which in turn is a continuation of application Ser. No. 07/155,953, filed Feb. 12, 1988, now abandoned.

FIELD OF THE INVENTION

This invention relates to in vitro determinations of the rate of blood clotting, particularly to bleeding time tests.

RELEVANT ART

The bleeding time determination is an important test frequently performed before major surgery. The conventional bleeding test time is performed by placing a blood pressure cuff at 40 mm Hg on the patient's arm and cutting an incision of standard size into the surgery patient's arm. The time for the blood to form a clot, thereby stopping the flow of blood, is measured using a stop watch. Normal values are between one to six minutes. This wide range renders the test inaccurate and insensitive. Furthermore, the test necessarily causes pain and scars the patient's arm.

Blood clotting is a complicated process that requires various proteins called coagulation factors in the plasma and subendothelium, as well as cells called platelets. The platelets adhere and aggregate at the site of the wound for proper clotting. The bleeding time test measures the total effect of all the factors working in concert. If the bleeding is prolonged, the test will not provide information to the clinician differentiating between, for example, platelets not adhering and the absence of a coagulation factor.

The vessel wall has several layers. The innermost layer, that which is in contact with the flowing blood, is made of endothelial cells. These cells prevent platelets from adhering. The outer layers are called the subendothelium, and contain collagen and other proteins which promote platelet adherence. As more and more platelets adhere, an aggregation of platelets forms, plugging a hole in the vessel, and promoting the coagulation factors to form fibrin. The cut vessel also releases factors causing the vessel downstream to constrict.

There are two tests which measure function of plasma coagulation factors. There are thirteen different coagulation factors divided between two pathways which are triggered by two different substances. The end result is fibrin, a fibrous protein that interweaves between the aggregated platelets.

A first test measures the cascading pathway known as the extrinsic pathway. This test is the prothrombin time (abbreviated-PT). A second test measures the intrinsic pathway and is called the partial thromboplastin time or PTT. The PT and PTT tests are performed on every patient going to surgery. If one of these tests is abnormal, one does additional tests looking for a factor(s) deficiency. These are routine tests currently performed in the medical laboratory.

Platelet function studies are performed by three routine methods: platelet adhesion, platelet aggregation, as well as the, in vivo bleeding time test, as herein previously described.

Platelet adhesion is measured by pushing blood through a plastic tube filled with tiny glass beads. The beads serve as foreign material which the platelets stick to. The platelet count is measured prior to passing blood through the column and after leaving the column and reflects the percent platelets retained. Although the glass bead column was commercially produced the results were too unpredictable causing it to be removed from the market.

A test performed by the medical laboratory is the platelet aggregation test. This test comprises platelet rich plasma separation form the patient's body. The platelet rich plasma is placed in a spectrophotometer to measure optical density. Aggregating agents (e.g. collagen, ADP, epinephrine, and ristocetin) are added and as the platelets aggregate the optical density decreases with time. Aggregation studies aren't exact and do not replicate the formation of a platelet plug at the site of a cut vessel.

Therefore, it would be advantageous to have an in vitro test that more accurately mimics what occurs at the site of a wound. Then the blood could be obtained by conventional blood gathering techniques and the bleeding time conveniently measured.

Another advantage is that an in vitro test can be far more standard than an in vivo test. Variables such as depth of wound, length of wound, blood pressure of the patient, and location of the wound on the patient's body are all automatically compensated for since the test is independent of the patient's body, leaving only the variable of primary concern, the clotting ability of the patient's blood.

Another advantage is that specific blood clotting factors can be systematically excluded from the test, thereby testing each variable individually. The PT and PTT tests can therefore be augumented, and perhaps replaced.

SUMMARY OF THE INVENTION

An aspect of this invention is an apparatus to measure bleeding time comprising:
 a container for blood having sides;
 sides defining at least one window;
 a top opening relatively larger in area;
 a bottom opening relatively smaller in area; and
 a clot-promoting material covering said window and defining at least one slit.

Another aspect of this invention is a method for determining bleeding time comprising:
 passing whole blood through a slit of known size cut in a clot promoting material; and
 measuring the period of time from the start of flow of blood through the slit to the cessation of blood flow through the slit.

BRIEF DESCRIPTION OF THE DRAWING

The Figure shows a perspective view of one embodiment of the present invention.

DETAILED DESCRIPTION

Bleeding time is a test done to a surgical patient before major surgery, for example, heart bypass or kidney transplant procedures. Hereinafter "the patient" will refer to that patient being tested.

Referring to FIG. 1, a tube 10, having a larger top end 12 and a smaller bottom end 14, is attached to a laboratory clamp 16. The laboratory clamp is attached to a vertical laboratory support bar 18. The tube is mounted so that the line defined by the center of larger top end and the center of the smaller bottom end is vertical. The tube has a rigid body having sides that define at least one window 20. The tube is preferably made from plastic, for example, polyethylene, or from glass. The primary criterion of a good tube material is that it not provoke clotting.

The tube has a larger top end, which provides an entrance for the blood, and constricts to a smaller exit. The tube is constricted to mimic the behavior of blood vessels downstream from an incision in the wall of the vessel. The constriction increases the pressure at the site of the cut, thereby increasing the shear stress of the blood as it flows through the opening. In a blood vessel, the opening is a wound; in the apparatus of this invention, it is the slit. Increased shear stress tends to increase the efficiency of platelet adhesion and aggregation.

Material 21 that promotes platelet adhesion and aggregation covers the window. The material defines at least one slit. Especially preferred is nylon that has been impregnated with collagen and coagulation factors. However, any fabric or other material that promotes clotting of blood in a reproduceable manner can be used. A collection device under the smaller end allows collection of blood. A slit 22 is cut into the material.

The top of the tube 24 is adopted to receive a syringe lock. The syringe lock is connected by a conduit 26 to a syringe 28, containing an amount of the patient's blood. The syringe is clamped by a clamp 30 to an automatic syringe plunger depression device 32. A piston 34 urges the syringe plunger 36 inwardly forcing blood through the connecting conduit and into the tube. The syringe can be connected to the top end of the tube directly. Then a weight can be placed on the syringe plunger.

The tube can hold a quantity of blood. An amount of the patient's blood enters through the larger top end of the tube. The blood then drains simultaneously through both the smaller bottom end and the slit to a blood collection device 38. As the blood escapes from the slit the material promotes platelet adhesion and aggregation, slowing the flow of blood through the slit. Eventually blood stops flowing through the slit. The time measured by timing means 23, from the first appearance of blood through the slit to the time the flow stops is measured. That is defined herein as the "bleeding time".

In conventional tests, the slit can be cut either horizontally or vertically in the patient's arm. In the practice of this invention, however, it has been found that horizontal slits provide the best and most repeatable results.

The time required for the blood to stop bleeding from the slit may not be the same as the amount of time required for the same size slit to stop bleeding on a patient's arm. However, the bleeding times obtained by the use of this invention correlate well to the in vivo times.

The pressure required to maintain a constant flow of blood from the syringe increases as flow through the slit becomes increasingly restricted. This is to be expected since, in effect, the blood is exiting through a continuously decreasing area. It is necessary to insure that blood passing the lower end will not clot. Therefore, any pressure buildup is entirely due to increased blockage of the slit.

A constant pressure can be provided by a weight urging the plunger downwardly. In one embodiment, the weight and the plunger form a piston. The weight provides a constant pressure on the blood. The weighted column of blood is forced through the smaller bottom end and the slit as the weight drops. As the blood forms a clot at the slit, the weight drops less rapidly. Therefore, it is possible to detect when blood has stopped flowing from the slit by measuring the rate at which the weight falls.

This can be done automatically. A sensor that measures rate of linear movement is attached to the weight. When the rate of lowering reaches a certain predetermined rate, or when the change in the rate of lowering stops, the test is over.

The decrease in flow rate can be easily measured. A quantity of blood in a syringe is slowly expelled by an automatic syringe depressor. The device can be made to be either constant pressure or constant speed. In a constant pressure device, the rate of the plunger is slowed and measured. In a constant speed device, the pressure rise inside the plunger is measured. In each case, when the measured variable reaches a constant level, the time is taken. It is preferred that the blood be pressurized by a known amount.

It is preferred that the diameter of the larger end of the tube be between about 0.25 cm to 1.5 cm and the diameter of the smaller end be about 0.5 mm to 2 mm.

From about 2 to about 10 ml of blood are necessary for the method of this invention. The blood is collected in a 10 ml tube with citrate as anti-coagulant. No other preparation is needed or appropriate. If the blood is collected in a syringe, it can be utilized from the syringe directly.

The blood that has been placed in a syringe is forced from the syringe by activating its plunger. The end point of the test can be identified by keeping the blood under constant pressure and noting when the speed of the plunger is consistent with a closed slit.

The platelet plugging of a cut vessel correlates to the test method described in this invention. The lining endothelial cells are damaged, releasing substances into the blood stream causing constriction of the vessel distal to the cut. This has a damaging effect elevating intravascular pressure and increasing flow through the open cut. This increased flow causes more platelets to reach the cut which adhere to the vessel. The platelets plug the cut vessel by activating many other platelets flowing by which pile-up or aggregate and promote a clot.

The device described here imitates a cut vessel. Blood flows through a plastic cylinder (resembling a normal vessel) which then narrows (resembling constriction of the vessel distal to a cut). Above the constricted section is thin material coated with all the necessary proteins found in the subendothelium of a vessel. This material has a cut allowing blood to flow through it under pressure. The platelets adhere to the cut portion, clump and close off the cut material. This test is timed from the beginning of blood flow through the cut, until it clots or no blood flows through the cut. This test measures platelet adhesion and aggregation in one easy step and duplicates the in vivo bleeding time. However, this bleeding time is accurate, well controlled, and reproducible, unlike the in vivo bleeding time.

The description above describes the currently preferred embodiment. It is important to realize that the invention is broader than this embodiment. In the test described, platelet adhesion and aggregation are the only aspects of the coagulation process measured. That is because the cryoprecipitate that is added to the slit material provides all the other factors needed for blood coagulation. It would be possible, for example, to measure the platelet adhesion and aggregation ability of a hemophiliac's blood. After a period of time, it would stop bleeding because the factors that would be missing in the hemophiliacs natural blood are artificially supplied.

An aspect of this invention is the diagnosis of the nature of the disease in patients exhibiting prolonged bleeding times. This is done with a panel of bleeding tubes, as herein described. Each slit material has all factors but one. The nature of the disease can be found by determining which tube exhibits a bleeding time that is significantly longer than the panel. The factor missing is that slit material is also missing in the patient's plasma.

Use of this technique can rapidly pinpoint blood deficiencies that can be quite rare. The patient can benefit by having a treatment tailored for his particular disease.

In the procedure described, the bleeding time will be prolonged only if there is a deficiency in platelet adhesion and aggregation. Such deficiencies can be inborn, but are more commonly found as a result of alloimmunization in patients who may have received multiple transfusions.

The information the test provides can be used as a binary benchmark for major surgery. If the test is negative, the treatment may be modified by transfusing platelets more immunologically compatable with the patient. Then the test can be periodically repeated until it is positive.

Uses for the invention described herein include use as a diagnostic test, a screening test, a test to monitor platelet therapy, a test for screening blood donors, and a test for monitoring antiplatelet drugs.

When used as a diagnostic test, von Willebrand's disease can be detected and therapy monitored. The in vivo bleeding time will be replaced with this new test. Platelet defects can be diagnosed in patients with uremia and therapy monitored in these patients. Congential platelet defects can be diagnosed such as Glanzman's thrombosthenia, Bernard-Soulier syndrome, and gray platelet defect and other coagulation factor deficiencies can also be diagnosed.

As a screening test, the in vitro bleeding time will also be useful in screening surgery patients for bleeding tendencies. It will be a useful adjunct screening test or possibly replace the PT and PTT. Currently cardiovascular surgeons use the in vivo bleeding time as a screening test. The in vitro bleeding time can replace this test.

There are no tests to accurately measure the effectiveness of platelet transfusions. The only test used at the present time is platelet counts before and after platelet transfusions. The in vivo bleading time measures platelet function after the platelets are infused and determines the number of platelet transfusions required for particular patient.

Platelet concentrates are prepared from healthy persons donating blood. Many times these persons have taken aspirin or other medications which effect platelets function, but they fail to report in the interest of giving blood as a public service. No function tests are performed on the platelets prepared from these donors to utilize for platelet transfusions. This test is useful for this purpose. The in vitro bleeding time could also evaluate the collection and storage of platelets to be used for patients.

Antiplatelet drugs are used in patients who have had stokes, heart attacks, and diabetes. Aspirin and persantin are the two drugs most commonly used. This test will be useful to monitor the drugs, since individual variation frequently occurs. It may also be useful for monitoring any future antiplatelet drugs.

The collagen membrane useful as the slit membrane is made by dissolving 0.02-0.10 Grams of Type III soluble in collagen about 10 ml of 0.05-0.2 percent glacial acetic acid. This solution can be prepared in advance and cold stored at 4° C. until ready for use. A basic solution is made when 0.5-2.0 ml of the Type III collagen solution is then mixed with about 0.1 ml of 0.5-2.0 N sodium hydroxide. A 1-cyclohexyl-3-(2-morpholinoethyl)-carbodiimide metho-p-toluenesulfonate (hereinafter "CDI") solution is made when equal amounts of the basic solution and CDI solution having a 1.5 to 6 mg CDI/ml in saturated saline are mixed together.

A Nylon Macro Filter having 40-100 micrometer openings is cut into conveniently sized square sections. The squares of the filter material are laid flat and each is coated with 1 ml of the CDI collagen solution. Type I collagen can then be spread over the surface of the CDI collagen III-coated membrane. It is convenient to sprinkle powdered Type I collagen powder over the surface of the membrane.

The membrane is allowed to dry at room temperature until moist. This typically takes about 1.5 hours. Preferably, eight to ten drops of cryoprecipitate are carefully applied to membrane surface. The membrane so prepared is then preferrably placed collagen side down, left at room temperature to dry for 35 minutes to one hour, and the unprepared filter surface is prepared in identical manner.

The filter is then dried at between about 15° C. and 30° C. for between about 1.5 to 3 hours. It is important that the membrane be moist. When dry, the membrane edges begin to retract. If the membrane has been coated on both sides, only one side is prepared as follows. A solution of about 10 mg Calcium Chloride per ml water is added to the moist membrane until the membrane is saturated. This is typically about 0.3 ml of solution. Then 1.0 ml of thawed cryoprecipitate, preferably made by the procedure of E. R. Burka et al., Transfusion, 15, page 307 (1975), is overlaid on the saturated membrane and evenly dispersed. An unprepared square of nylon filter of the same size as preferably having smaller pores than the filter already used. Nylon filter is then carefully placed on top of the cryoprecipitate.

The cryoprecipitate from normal plasma may be substituted with specific blood factors. By such substitution various blood factors can be specifically deleted, thereby allowing testing for specific disorders of the blood. 10 mg/ml calcium chloride solution is used to cause clotting of the cyroprecipitate.

The membrane is dried at 30° C.-45° C. for between 15 minutes and 1 hour. The dried membrane is then placed in the refrigerator. It should be refrigerated at least 15 hours, but can be refrigerated until use.

Plastic or glass tubing between about 10 cm and 15 cm long and about 10 mm diameter is heated in the center with a flame. When the tube softens, it is gently pulled apart. The tube is gently blown into, creating a bulge immediately before the thinning of the tube created by drawing the tube. The inner diameter of the drawn section of the tube should be less than 1.0 mm internal diameter preferably between 0.05 mm and 1.0 mm. The tube is then cut at the thinned section.

The large end of the tube is heated, softening until a male half of a syringe lock can be inserted. The tube is formed by the insertion and then cooled and the narrow end trimmed. A window is cut into the blown bulge, and the walls of the tube defining a window about 6 to 8 mm×4 to 6 mm.

Of course, the tube can be made by drawing, blowing, and windowing the tubes with an automatic machine.

A membrane, as prepared in Example 1, is then placed over the window and glued on with epoxy.

The membrane is prepared so that the two sides are preferably not identical. The side that was created from the original filter is the inside. Therefore, if the doubly coated and larger pore size is the inside, a doubly coated membrane presents a collagen surface to the blood in the tube. The surface can be thought of as an artificial blood vessel with the endothelial cells removed.

10 Milliliters of a patient's blood is taken up in a syringe. The syringe is mated to a tube prepared as in Example II. The syringe plunger is placed under a known amount of weight. The entire apparatus is positioned upright and a horizontal slit 0.5 cm long is cut in the membrane.

It is greatly preferred that the slit be cut horizontally. However, small razor thin horizontal cuts in the membrane may be almost closed by the mechanical action of the membrane. It is therefore, preferred that a known amount of bending be incorporated into the membrane as it is mounted to open the slit.

The rate at which the syringe plunger falls is monitored. The bleeding time is that amount of time required before the plunger falls at a constant rate.

EXAMPLES

Example 1

Collagen Membrane

The collagen membrane useful as the slit membrane can be made as follows;

Type III collagen (Sigma Chemical, St. Louis, Mo.) solution was made by dissolving 0.05 Grams of Type III collagen in 10 ml of 0.1 percent glacial acetic acid. A basic solution was made by mixing 0.9 of Type III collagen solution with 0.1 ml of 1N sodium hydroxide. A CDI (Sigma Chemical, St. Louis, Mo.) solution was made when 1.0 ml of the basic solution is mixed with 1.0 ml of a 3 mg CDI/ml of saturated saline.

A Nylon Macro Filter having 60 micrometer openings and being 55 micrometers thick was cut into 5.0×5.0 cm square sections. The squares of filter were laid flat and each was coated with 1 ml of the CDI solution. Type I collagen (Sigma Chemical, St. Louis) was then spread over the surface of the CDI collagen III-coated membrane by sprinkling powdered Type I collagen.

The filter was then dried at room temperature for between about 2 hours. It is important that the membrane be moist. If the membrane is dry, its edges begin to retract. Visual checks are made periodically to observe moisture content.

A solution of 10 mg Calcium Chloride per ml water was added to the moist membrane until the membrane was saturated. About 0.3 ml of solution was used to saturate the membrane. Then 1.0 ml of thawed cryoprecipitate was carefully overlaid on the saturated membrane and evenly dispersed. An unprepared 5.0×5.0 cm square of nylon filter having pores 10 micrometer and being 45 micrometers thick was then carefully placed on top of the cryoprecipitate.

The membrane was dried at 37° C. for 30 minutes. The dried membrane was then placed in the refrigerator. The membrane was refrigerated for 15 hours and then cut and mounted on funnel tubes.

Example II

Making the Bleeding Time Tube

Plastic tubing about 5 mm in inner diameter, having one end closed, and about 10 cm long was heated in the center with a flame. When the tube softed, it was pulled apart. A bulge was created immediately before the thinning of the tube created by drawing the tube by gentle blowing while the tube walls were still soft. The inner diameter of the small section of the tube was less than 1.0 m internal diameter. The tube was then cut at the thin part of the tube.

The large end of the tube was heated and softened until a male half of a syringe lock could be inserted. The molded tube was then cooled and the narrow end trimmed to about 3 cm long. A window was cut into the blown bulge to define a window about 6 mm×4 mm large.

A membrane, as prepared in Example 1, is then placed over the window and glued on with epoxy. The inner portion of the membrane, having 60 micrometer pores, was mounted inwardly. After the glue has set a horizontal slit 2 mm to 5 mm long was cut with a razor.

Example III

Sample Blood Clotting Time Determination

10 Milliliters of a patient's blood was taken up in a syringe. The syringe was mated to a tube prepared as in Example II. The syringe was mounted vertically with a lab clamp. A 250 gram to 500 gram weight is placed on the syringe plunger. The rate at which the syringe plunger fell was monitored. The bleeding time can be calculated by noting when the rate the plunger falls becomes constant.

I claim:

1. An apparatus for measuring in vitro bleeding time comprising:
   a container for blood having an upstream portion communicating with a source of blood providing blood access to the interior of the container, sidewalls having at least one side opening, and a downstream opening downstream of the side opening having a relatively smaller cross-sectional area than that of said upstream portion, said downstream opening allowing blood to flow out of the interior of the container without clotting said downstream opening;
   a clot-promoting material covering said side opening and defining at least one slit, said slit constructed so as to allow blood to pass therethrough and out of the interior of the container until it is clogged, the arrangement of the container having a downstream opening with a relatively smaller cross-sectional area than that of the upstream portion causing an increased shear stress of the blood as the blood flows out of the container; and
   means to measure a period of time for blood to clot in the vicinity of said slit, wherein said period of time is correlatable to the period of time required for the patient's blood to clot in an in vivo bleeding time test.

2. The apparatus of claim 1, wherein said clot-promoting material comprises a filter material coated with collagen.

3. The apparatus of claim 1, wherein said clot-promoting material comprises an inner nylon filter having a pore size of between 5 and 100 micrometers, coated with collagen with a cryoprecipitate added, interfacing with an outer nylon filter having a pore size of 5 to 20 micrometers.

4. The apparatus of claim 1, wherein said source of blood is a syringe containing blood, communicating with said upstream portion.

5. The apparatus of claim 4 further comprising an automatic syringe emptying device, said automatic syringe emptying device engaging with said syringe so as to operate a plunger of said syringe.

6. The apparatus of claim 2, wherein said collagen contains blood clotting factors normally found in plasma.

7. The apparatus of claim 6, wherein said blood clotting factors in the collagen are provided by cryoprecipitate.

8. The apparatus of claim 5, wherein said automatic syringe emptying device is constructed so as to empty said syringe at a constant speed.

9. The apparatus of claim 8, further comprising a pressure sensor, said pressure sensor positioned and arranged so as to sense the pressure required to depress said plunger of said syringe at a constant rate, thereby allowing the in vitro bleeding time to be determined.

10. The apparatus of claim 8, wherein said automatic syringe emptying device is positioned and arranged so as to operate said plunger to empty said syringe at a rate such that the pressure remains constant on said plunger of said syringe.

11. The apparatus of claim 10, including a sensor positioned and arranged so as to detect the rate of movement of said plunger of said syringe, thereby allowing the in vitro bleeding time to be determined.

12. A method for determining in vitro bleeding time, comprising the steps of:
flowing whole blood downstream from an opening port through at least one channel and past a side opening in a side wall of said channel covered by clot-promoting fabric having a slit of predetermined dimensions formed in said fabric, said slit allowing blood to escape therethrough out of said channel, said channel narrowing below said opening port and said slit and having a discharge port which is smaller than said opening port below said slit;
discharging the blood through said discharge port; and
timing the period of time from when the blood starts to flow through said slit to when the blood ceases to flow through said slit, the time period being the in vitro bleeding time.

13. The method of claim 12, including the step of pressurizing the whole blood to a selected pressure.

14. The method of claim 12, including the step of promoting clotting of said blood in the vicinity of said clot-promoting fabric, said fabric including collagen.

15. The method of claim 12, including the step of:
placing the whole blood in a syringe having a plunger;
depressing the plunger into the syringe at a selected and constant pressure; and
identifying the time at which blood no longer escapes from said slit by monitoring the rate at which the plunger is depressed into said syringe.

16. The method of claim 12, including the step of promoting clotting of said blood in the vicinity of said clot-promoting fabric, said fabric including a cryoprecipitate.

17. The method of claim 12, wherein said at least one channel comprises a plurality of channels and, further comprising the steps of:
flowing whole blood through said plurality of channels, the clot-promoting fabric covered side opening of said channels having a cryoprecipitate, wherein said cryoprecipitate in each said plurality of channels is lacking at least one of thirteen different coagulation factors found in normal human blood; and
comparing the bleeding-time periods between each of the channels to identify which if any of the thirteen coagulation factors from the blood is missing, wherein the whole blood placed in the channel with the longest bleeding time is lacking said at least one factor missing from the cryoprecipitate of that channel.

* * * * *